United States Patent [19]

Grangeat et al.

[11] Patent Number: 5,333,107
[45] Date of Patent: Jul. 26, 1994

[54] PROCESS AND APPARATUS FOR THE RECONSTRUCTION OF THREE-DIMENSIONAL IMAGES OF AN OBJECT USING TWO PATHS HAVING A COMMON AXIS

[75] Inventors: Pierre Grangeat, Saint Ismier; Patrick Le Masson, Villard de Lans, both of France

[73] Assignee: Commissariat A L'Energie Atomique, France

[21] Appl. No.: 788,172

[22] Filed: Nov. 5, 1991

[30] Foreign Application Priority Data

Nov. 29, 1990 [FR] France ............................. 90 14957

[51] Int. Cl.[5] .............................................. G06F 15/42
[52] U.S. Cl. ................................................ 364/413.19
[58] Field of Search ...................... 364/413.19, 413.13, 364/413.20, 413.15; 378/145, 146, 161

[56] References Cited

U.S. PATENT DOCUMENTS

| | | | |
|---|---|---|---|
| 4,651,002 | 3/1987 | Anno | 250/358.1 |
| 4,696,022 | 9/1987 | Sashin et al. | 378/41 |
| 5,032,990 | 7/1991 | Eberhard et al. | 364/413.13 |
| 5,124,914 | 6/1992 | Grangeat | 364/413.16 |
| 5,175,773 | 12/1992 | Garreau et al. | 364/413.19 |

FOREIGN PATENT DOCUMENTS

| | | |
|---|---|---|
| 0292402 | 5/1988 | European Pat. Off. |
| 0379399 | 1/1990 | European Pat. Off. |
| 2088670 | 6/1982 | United Kingdom |

Primary Examiner—Donald E. McElheny, Jr.
Attorney, Agent, or Firm—Pearne, Gordon, McCoy & Granger

[57] ABSTRACT

A process for reconstructing three-dimensional images of an object with the aid of measurements performed by bidimensional arrays of sensors on a succession of incidences around the object. There are at least two circular coaxial paths (2,2') on which the arrays (4,4') are displaced. Thus, it is possible either to accelerate the taking of images, or increase the volume of the measurements, or accelerate the calculation of the reconstructed image, through the use of a single reference frame in whose coordinates the sums of the measurements on each sensor are characterized. The process has particular application to medical imaging or to the non-destructive inspection of parts in emission or radiation attenuation tomography.

6 Claims, 3 Drawing Sheets

PROCESS AND APPARATUS FOR THE RECONSTRUCTION OF THREE-DIMENSIONAL IMAGES OF AN OBJECT USING TWO PATHS HAVING A COMMON AXIS

BACKGROUND OF THE INVENTION

The invention relates to a process and an apparatus for the reconstruction of three-dimensional images of an object involving measurements on two circular paths having a common axis, i.e. the paths belong to parallel planes and their centres are joined by an axis perpendicular to the plane of the paths. If the planes of the paths coincide, they are concentric. It is also possible to envisage more numerous paths.

The reconstruction of images relates to a given object to be examined and the means used comprise two dimensional arrays of sensors each traversing one of the paths or, in an equivalent manner, a single array which traverses all the paths.

The image of the object is defined by values assumed by a function on each of its points. The function is also a property of a radiation (e.g. X or gamma) having a conical shape and with a focal point and which passes through the object. Each ray is received by one of the sensors of the bidimensional array and consequently represents the sum of the function on all the points of the object belonging to said ray. An appropriate processing of the sums on all the rays for an adequate number of measurements in accordance with different incidences around the object makes it possible to reconstitute the image of the object.

In practice, consideration is only given to finite numbers of rays and points of the object in accordance with discretizations or interconnections.

The present invention relates to an improvement to an earlier invention described in European patent application EP-A-0292 402, but it is possible to envisage the use of tile present invention in other circumstances or using other mathematical data processing methods.

The methods which can be envisaged in particular use what is called the Radon transform of the function to be measured, which is defined as the sum of the function on each of the planes, called Radon planes, which pass through the object in question or, even better, the primary derivative of said transform. The contribution of the points of these planes which do not belong to the object are considered to be non-existent, which is valid in the case of a radiation passing through an ambient gaseous medium without being attenuated. Here again, a discretization is performed in order to only perform the calculations on a finite number of planes.

The primary derivative of the Radon transform is defined as being the derivative of the Radon transform as a function of the variable $p$ defining the distance from the plane in question to an origin. For each plane, it corresponds to the sum on said plane of the primary derivative of the Radon transform in the direction perpendicular to the plane. The invention described in EP-A-0292 402 demonstrates that for a plane passing through one position of the focal point of the radiation cone and encountering the bidimensional array of sensors, it is possible to calculate on the basis of measurements the exact value of the primary derivative of the Radon transform on said plane. This calculation, in accordance with the formulas given in EP-A-0292 402, makes use in preferred manner of a focal point distance correction weighting, two filtering operations corresponding to the calculations of the primary derivatives respectively along the rows and columns of the array of sensors, two summations along the intersection line between the plane to be processed and the bidimensional array of sensors and then a linear combination and standardization of the results. This summation makes use of the necessary interpolations, because these intersection lines pass between the rows of sensors or intersect them.

Throughout the remainder of the application, the sum is understood to mean the weighted sum of the measured values (in the case of the Radon transform), as well as the linear combination of the sums of weighted and filtered values (in the case of the primary deriratire of the Radon transform) obtained along the array rows and columns.

The sum of the function on the points of the Radon planes is easy to obtain, provided that these planes have an intersection with the bidimensional array of sensors and pass through the single focal point aimed at by the sensors. It is sufficient to form the sum of the values measured by each sensor located at the intersection, with the necessary interpolations, because the intersections of the Radon planes pass between rows of sensors or intersect them. Once the values of the function on the Radon planes have been calculated, inversion formulas exist and which are described in the aforementioned patent application, which make it possible to arrive at the values of the function on the points of the interconnection of the object corresponding to the image to be reconstructed.

However, it is necessary to return to conditions making it possible to obtain an adequate number of Radon planes to permit a satisfactory description of the object. Each Radon plane can be defined by what is called its characteristic point, i.e. the projection point on said plane of an arbitrarily chosen origin 0. This characteristic point, designated C in FIG. 1, can be defined by its spherical coordinates $p$, $\phi$ and $\theta$ of ray, longitude and colatitude respectively on the basis of the origin 0. The Radon plane P passing through the characteristic point C can be defined by the radius $p$ and the unitary vector $\vec{n}$ of direction $\overrightarrow{OC}$.

The values of the function on the Radon plane can only effectively be calculated for the Radon planes intersecting the path covered by the focal point of the radiation. In the case of an attenuation function, said focal point is specifically a point source of X, gamma and similar rays. This is the concept which is described in the aforementioned European patent application. The same geometrical conditions exist in emission tomography, when the function to be measured is the activity emitted by the body. The focal point then has no physical existence and simply corresponds to the convergence point towards which all the collimators used in front of the bidimensional array are directed. In order to obtain an adequate number of Radon planes, it is necessary to carry out several measurements with different positions of the focal plane.

On considering a circular path T covered by the focal plane (or the source) S, the planar array of sensors Pdet passing through the same path as the focal point S or possibly a concentric path with a different radius and it will also be assumed that the origin 0 used for defining the characteristic point C is located on the axis of the path T. The volume enveloping the characteristic points corresponds to a torus To produced by the rotation of a spherical surface of diameter OS around the rotation axis of the path T. Thus, the Radon planes passing through the focal point S have their characteristic points distributed over the spherical surface of diameter OS, because the angle SCO is a right angle. The torus To is called the characteristic volume of the measurements, which thus depends on the shape of the path T and its position relative to the origin 0.

It is also sufficient, in order to obtain a complete description of the object by processes using the sums of the function on the Radon planes, to be able to have characteristic points belonging to a characteristic volume of the object, which is always included in a sphere V centered on the origin 0 and which envelops the object M. Thus, it is certain that if the characteristic volume of the object is included in the characteristic volume of the measurements, it will be possible to reconstruct the image of the object M. In the case of a circular path T, this condition is unfortunately not fulfilled, because a shadow area remains for characteristic points of the sphere V not belonging to the torus To and whose Radon planes do not intersect the path T. Summary of the Invention

SUMMARY OF THE INVENTION

The essential object of the invention is to facilitate reconstructions by making them faster if several measuring sequences are used, which makes it possible to reduce the duration of examinations in medical imaging where the patient must remain stationary and in non-destructive inspection where working speeds are imposed. The process makes it possible to treat cases where each acquisition sequence is defined by individual parameters and in particular the case where the two centers of the trajectories of two acquisition sequences are close, but distinct for mechanical reasons.

It is then the quality of the images which is improved. Finally, when the two circular paths are on either side of the object, the shadow area can be reduced and the image further improved. The superimposing of several paths also makes it possible to increase the characteristic volume of measurements and authorizes the examination of larger objects. However, in all cases there are calculation problems, because the pooling of acquisitions made on several paths requires conversions utilizing mathematical operations due to the parametrization of each series of measurements by individual characteristic coefficients.

Moreover, if use is made of different measuring sequences and if the sums of the function are firstly produced in separate reference frames, the mechanical imprecisions on the real orientation of the sensors, the real radii of their path and the focal point, etc., lead to supplementary calculations and interpolations when the reference frame changes are carried out for pooling the results of series of measurements. Thus, there are deteriorations to the image reconstruction informations. However, if use is made of the process according to the invention, the parameters of the paths and the series of measurements, which integrate the mechanical imprecisions and which have been measured during preliminary calibrations of the machine are used directly in the reference frame employed for reconstructing the object, whose images will then be reconstructed with a greater clearness.

Thus, the invention is based on the finding that, if a common reference frame is defined for parametrizing the paths and the characteristic measurement volumes, there is no need for any conversion of coordinates or changes of reference frames in order to pool the results coming from different paths. Thus, there is a direct obtaining of the informations which are of interest in the object reference frame in which the interconnection used for reconstructing the images is defined. This procedure is easy if the paths are coaxial.

Thus, the invention relates to a process for the reconstruction of three-dimensional images of an object defined by values assumed by a function on points of the object, the function being a property of a conical radiation having a focal point and passing through the object, in which the function is calculated by means of sums of the function on planes passing through at least one point of the object and defined in an object reference frame, incorporating at least two series of measurements, each sum of the function on said parametrized planes in the object reference frame being calculated on the basis of at least one of the series of measurements, each of the series of measurements being performed with a bidimensional array of radiation sensors oriented towards the focal point and which is displaced around the object on a respective circular path, characterized in that the paths have centers joined by an axis perpendicular to the paths, are defined in the same way as the object by a relationship with an object reference frame, in that for each series of measurements, a series of sums of the function is calculated in its object reference frame for the planes secant or tangential to a path associated with the focal point and in that the series of sums of the function are pooled to obtain the sums of the function in said reference frame.

Advantageously, the object reference frame has an axis coinciding with the axis perpendicular to the paths. The coordinates used are advantageously spherical.

BRIEF DESCRIPTION OF THE DRAWINGS

The invention also relates to apparatuses designed specifically for performing the process.

The invention is described in greater detail hereinafter relative to non-limitative embodiments and the attached drawings, wherein show.

DETAILED DESCRIPTION OF THE PREFERRED EMBODIMENTS

Figure 1:
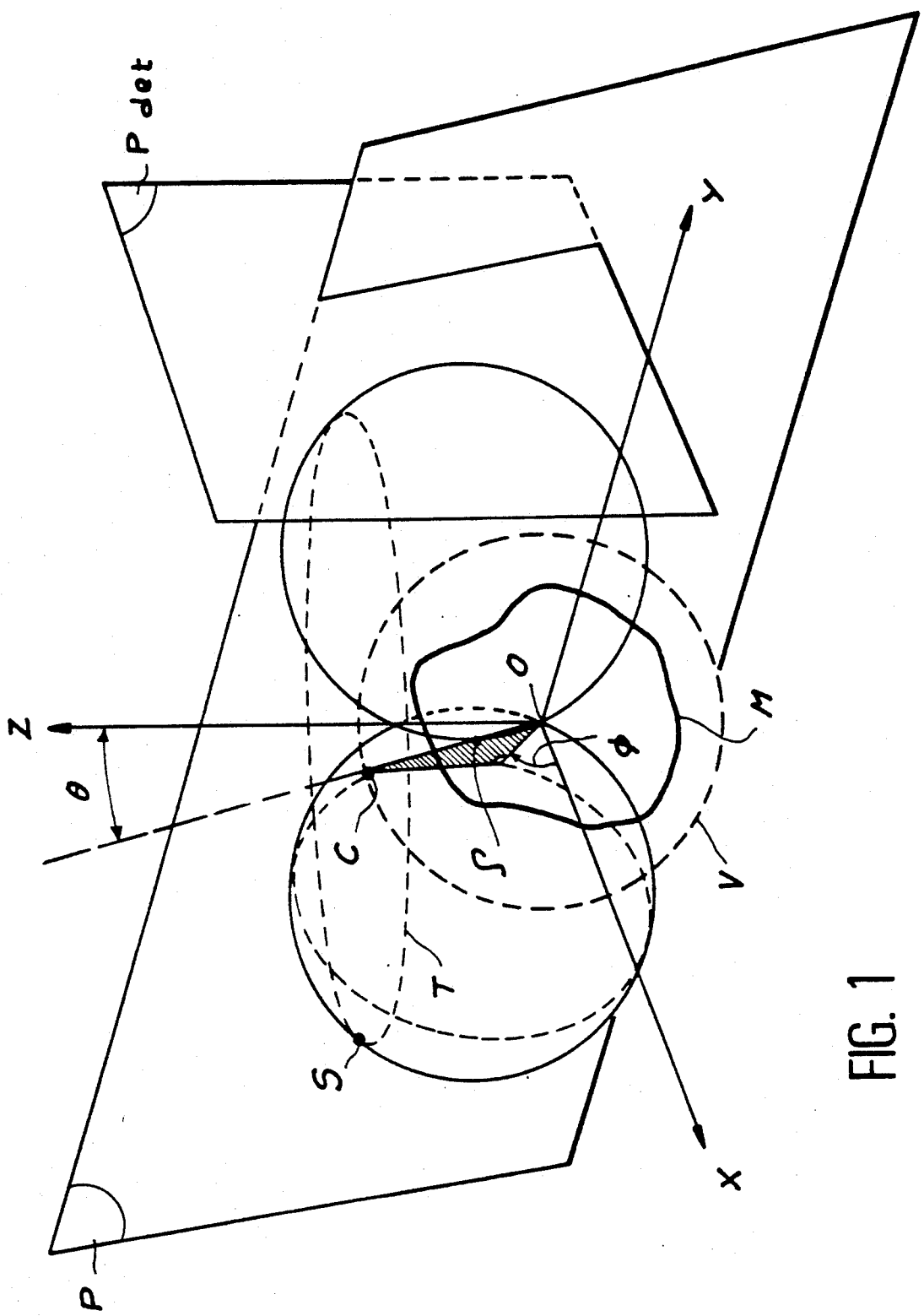
FIG. 1, already described, the geometrical conditions linked with acquisitions with the aid of circular paths.
Figure 2:
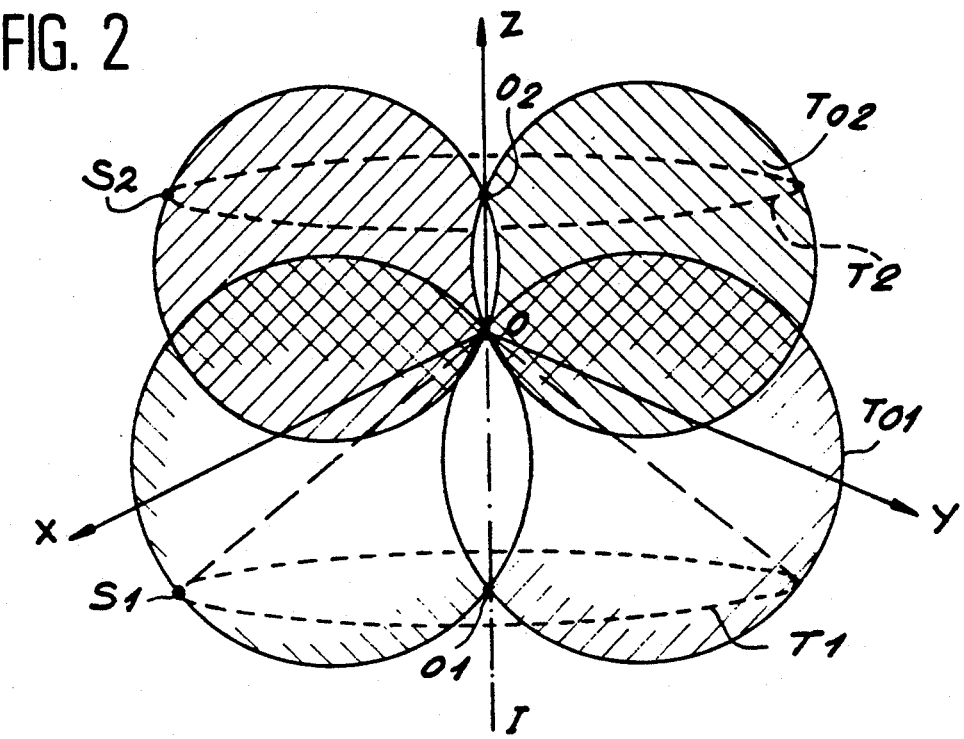
FIG. 2 a generalization of the geometrical conditions.

Consideration will now be given to FIG. 2, where the circular path T1 and of center 01 belonging to a plane passing at a distance from the origin 0 and in which said plane is perpendicular to the axis Z. The characteristic volume of the measurements, i.e. all the characteristic points of the Radon planes defined on the basis of the origin 0 is once again a torus To1 produced by rotating a spherical surface of diameter OS1 along the path T1 and around the origin O. The torus To1 has a complex shape, because it has an intersection portion I in the center, because the meridian section of the torus To1 form two overlapping circular surfaces. A simple geometrical reasoning makes it possible to ensure that the planes associated with the points located within the intersection zone I do not intersect the path and that said portion belongs to the shadow area. The characteristic volume of the measurement represented along said meridian section is that which is hatched.

What is shown is the superimposing of another torus To2 resulting from the rotation of a circle of diameter 0S2 around another path T2 of center O2 separate from origin 0 and which is here shown substantially in the center of the segment 0102. The characteristic volume of the measurements is also hatched. Thus, although these characteristic volumes do not coincide and the multiplication of the paths having a common axis makes it possible to describe more voluminous objects, there is still a shadow area around the axis Z. Therefore the process according to the invention is not suitable for perfectly describing the examined objects at this location, even if the volume of the shadow area is reduced. In practice, interpolations will be performed within the shadow area in accordance with the teachings of the earlier-dated invention.

Figure 3:
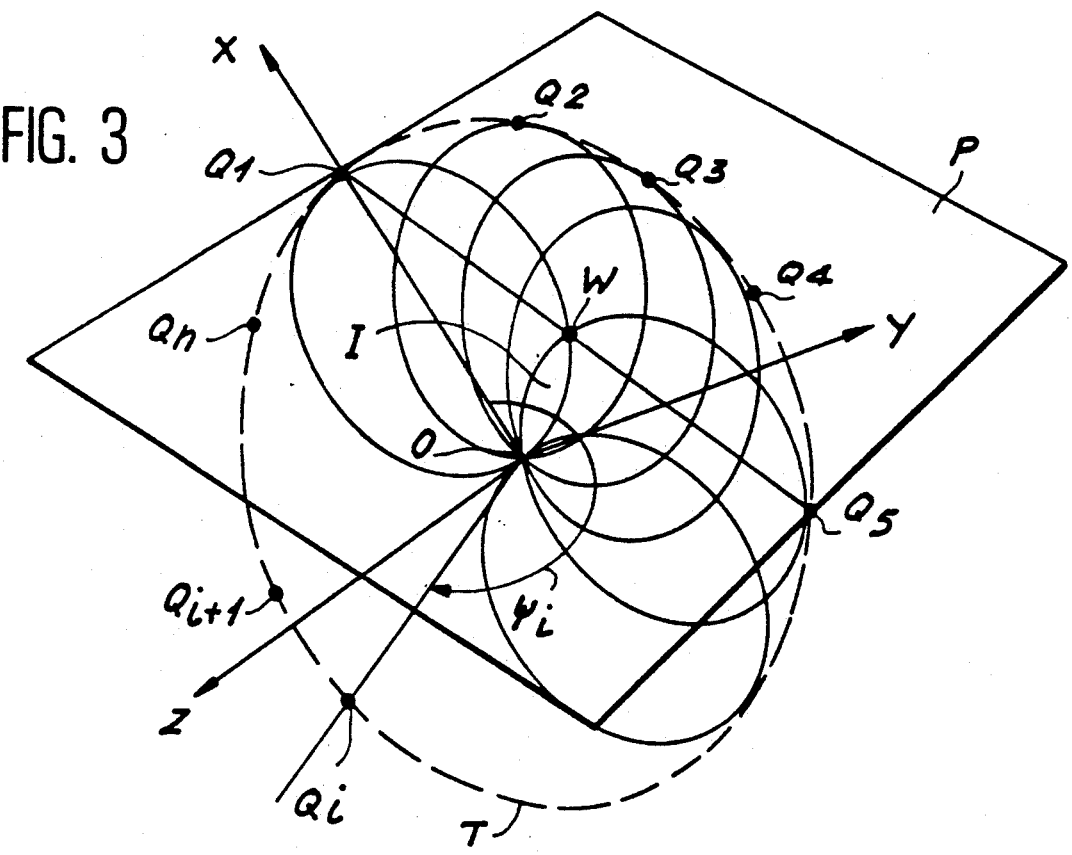
FIG. 3 a measurement acquisition procedure.

A possible procedure for performing the process is shown in FIG. 3. The two paths are combined into a single path T on which n measurements are performed at regularly distributed points Q1 to Qn defined by angles $$\psi i = \psi(i - 1) + \frac{2\pi}{n}$$

on the basis of the axis X. For each point Qi measurement takes place of the values of the function on the Radon planes, whose characteristic points belong to the sphere of diameter OQi. In the general case, the sum of the function on these planes can be calculated on the basis of two positions of the focal point, because these planes intersect the path T at two points, namely Q1 and Q5 in the considered example. In practice, the points W which are retained are points defined regularly on an interconnection defined in the reference frame O,X,Y,Z by regular spherical coordinates (radius $\rho$, longitude $\phi$ and colatitude $\theta$), although the Radon plane does not intersect the path precisely at the points Q and consequently approximations or interpolations on the angles $\psi$ i are necessary, in accordance with the method envisaged in the earlier-dated invention in an exemplified manner.

According to the present invention, there are two measuring sequences, whereof each simultaneously performs measurements on a subset of points Q. The two standard ways for carrying this out consist either of allocating uneven points to one and even points to the other, or subdividing the path into two equal halves, whereof the respective points Q are allocated to one of the measuring sequences, each subset then having half the points Q. It is therefore possible for the subsets will be larger than a half, which will render possible overlaps for certain points Q. Another idea consists of doubling the measurements at the points Q in order to improve the quality of the image by a statistical mean.

For each of the points of the characteristic volume of the object, the pooling of series of measurements e.g. consists either of alternatively considering the function sums associated with each series of measurements for the planes encountering the two paths of the focal points, or forming their means, or only considering an associated function sum when the plane only encounters one of the paths.

Figure 4:
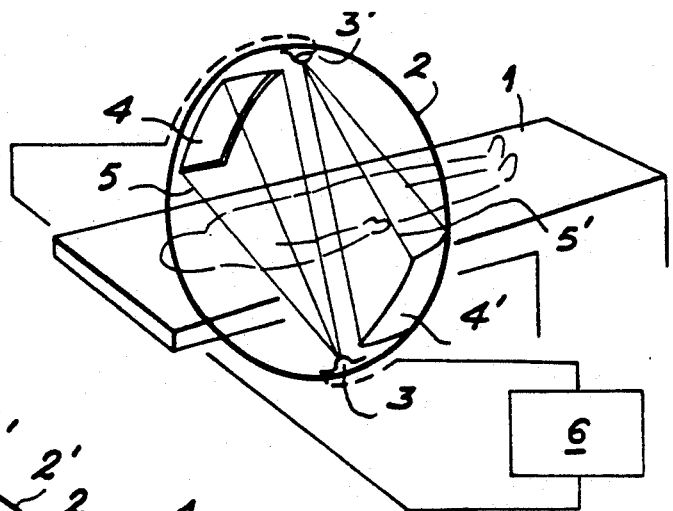
FIG. 4 an apparatus suitable for the acquisition of the measurements according to FIG. 3.

An appropriate apparatus is shown in FIG. 4. It is a medical tomography installation where the patient is lying on a horizontal table 1. A circular rail 2 extends in a vertical and transverse plane and surrounds the table 1. It is in fact a rack, which carries two mobile carriages which mesh thereon. These carriages are indicated diagrammatically and reference can be made to the earlier-dated invention for further technical details. Each of them carries an X-ray source in the vicinity of a screen carrying a bidimensional array of sensors. The sensors of the screen 4 are focussed on the source 3 of the other mobile carriage and those of the other screen 4' are focussed on the source 3' of the first mobile carriage. The sources 3 and 3' emit a conical beam 5 or 5'. The object to be examined is placed in the intersection zone of the cones of the two beams 5 and 5'. In operation, the two mobile carriages are simultaneously displaced in rotation so as to remain diametrically opposite. The movements are controlled by the installation control computer. In the case of an identical emission tomography installation, the sources 3 and 3' will be omitted and the focal point of the sensors of each screen 4 or 4' will advantageously be located in the center of the other screen 4 or 4' in order to simplify the acquisition calculations. It will then be possible to separate the sources 3,3' from the screens 4,4' in such a way that the beams 5 and 5' e.g. intersect at right angles. The screens 4 and 4' are connected to measurement acquisition and processing means represented in general terms by 6.

Figure 5:
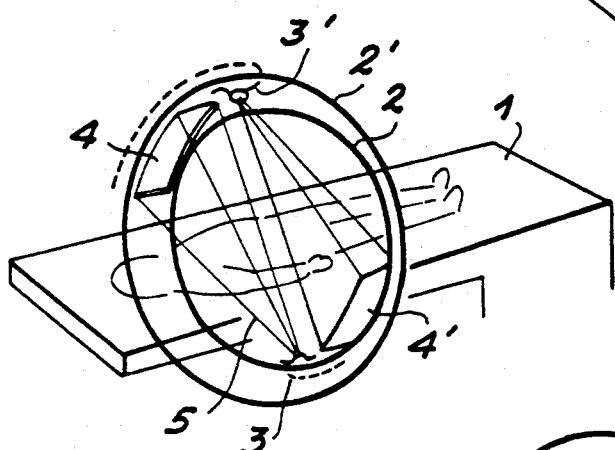
FIGS. 5 to 7 three more complex apparatuses which can be envisaged in conjunction with the invention.

A somewhat different design is shown in FIG. 5. The mobile carriages are identical to those described hereinbefore, but in this case are placed on a respective rail 2 or 2', which are coplanar and concentric. Nothing is modified with the exception of the coefficients of the geometrical magnification relations as a function of the distances of the sources 3 and 3' and the screens 4 and 4' from the origin 0.

Figure 6:
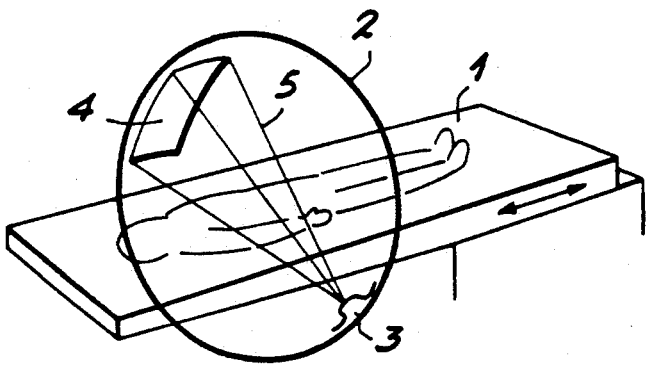

The invention can be performed (FIG. 6) with a single rail 2 carrying a single source 3 diametrically opposite to a screen 4 carrying a bidimensional array of sensors. In this design, the source 3 and the screen 4 perform two complete rotations between which the table 1 undergoes a translation perpendicular to the plane of the rail 2. Such a solution is used for increasing the characteristic volume of measurements in accordance with FIG. 2.

Figure 7:
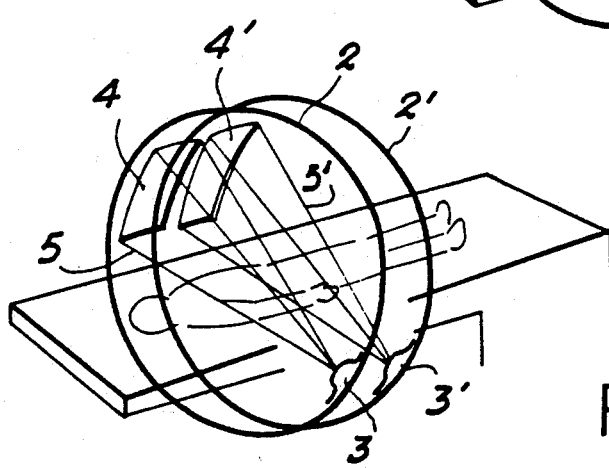

The same result can be obtained by doubling the apparatus (FIG. 7), so that two circular rails 2 and 2' each carry a source 3 or 3' and a screen 4 or 4'. The displacements on the two rails 2 and 2' are simultaneous, which speeds up the acquisition of measurements.

If the results for a given Radon plane are obtained at each path, a mean or an interleaving is carried out prior to performing the image reconstruction operations, such as the filtering, weighting and back-projection operations described in the earlier-dated patent.

The invention can be performed in other ways. Thus, the angular displacement on each circular path can be reduced to a circumferential portion. An advantageous case is that of a complete circumference formed by the union of angular displacements. It is in particular pointed out that more numerous paths are possible without passing outside the scope of the invention.

Moreover, particular consideration has been given to the use of this process for the inversion of the Radon transform or its primary derivative. It is possible to proceed in substantially the same way with a Fourier transform of all the radii of the Radon space not intersecting the shadow area and namely for each of the characteristic volumes of measurements. The pooling of the thus transformed measurements can be performed in said common reference frame.

Instead of the Radon transform or its primary derivative, it is also possible to proceed in the same way with the Hilbert transform.

The invention can be used in medical imaging or the non-destructive inspection of parts.

We claim:

1. A process for reconstructing a three-dimensional image of an object with at least one two-dimensional array of sensors, said image expressing a property, varying in the object, of a radiation, comprising the steps of:

moving the sensors in at least two trajectories around the object, said trajectories consisting of at least portions of circles having centers joined by a line perpendicular to planes in which the trajectories are comprised;

focussing the sensors of each array to a common focal point beyond the object so as to view a conical space, the focal point having a constant position with respect to the array of sensors;

taking measurements with the sensors consisting of sums of the property along rays passing through the object and directed to the focal point;

summing measurements of the rays belonging to summation planes to obtain summations associated with the summation planes, the summation planes being defined by coordinates in an object reference frame;

reconstructing the image by combining the summations.

2. A process for reconstructing three-dimensional images according to claim 1, wherein the line extends along an axis of the object reference frame.

3. A process for reconstructing three-dimensional images according to claim 1, wherein the property is an absorption property of the radiation, which is produced by point sources at the focal points.

4. A process for reconstructing three-dimensional images according to claim 1, wherein the property is an emission property of the radiation by the object.

5. A process for reconstructing three-dimensional images according to claim 1, wherein the trajectories consist of complementary parts of a single circle.

6. A process for reconstructing three-dimensional images according to claim 1, wherein the trajectories consist of two circles comprised in parallel planes.

* * * * *